(12) United States Patent
Koenig et al.

(10) Patent No.: US 7,821,640 B2
(45) Date of Patent: Oct. 26, 2010

(54) METHOD AND DEVICE FOR RECONSTRUCTING A THREE-DIMENSIONAL FLUORESCENCE OPTICAL TOMOGRAPHY IMAGE BY DOUBLE MEASUREMENT

(75) Inventors: Anne Koenig, Saint Martin D'uriage (FR); Lionel Herve, Villeurbanne (FR)

(73) Assignee: Commissariat a l'Energie Atomique, Paris (FR)

( * ) Notice: Subject to any disclaimer, the term of this patent is extended or adjusted under 35 U.S.C. 154(b) by 283 days.

(21) Appl. No.: 12/087,489

(22) PCT Filed: Jan. 12, 2007

(86) PCT No.: PCT/FR2007/000054

§ 371 (c)(1),
(2), (4) Date: Jul. 8, 2008

(87) PCT Pub. No.: WO2007/080326

PCT Pub. Date: Jul. 19, 2007

(65) Prior Publication Data

US 2009/0005676 A1 Jan. 1, 2009

(30) Foreign Application Priority Data

Jan. 12, 2006 (FR) .................................. 06 00286

(51) Int. Cl.
*G01N 21/25* (2006.01)

(52) U.S. Cl. ........................ 356/417; 600/476; 600/473; 600/425

(58) Field of Classification Search .................. 356/417; 600/425, 476, 473
See application file for complete search history.

(56) References Cited

U.S. PATENT DOCUMENTS 4,945,239 A 7/1990 Wist et al.
(Continued)

FOREIGN PATENT DOCUMENTS

EP 0 385 608 A1 9/1990
WO WO 99/20997 A 4/1999

OTHER PUBLICATIONS

Pogue et al., Comparison of Imaging Geometries for Diffuse Optical Tomography of Tissue, *Optics Express*, Optical Society of American, Washington, DC, vol. 4, No. 8, Apr. 12, 1999, pp. 270-286.
(Continued)

*Primary Examiner*—Tarifur Chowdhury
*Assistant Examiner*—Abdullahi Nur
(74) *Attorney, Agent, or Firm*—Oliff & Berridge, PLC

(57) ABSTRACT

To examine a plate-shaped object comprising fluorophores and having a first face and an opposite second face, the method comprises a first sequential illumination step of the first face of the object with a fluorophore excitation light and a first sequential acquisition step of a first series of images by detecting light emitted by the second face of the object. The density of the lighting points is lower than the density of the detection points and the method further comprises a second sequential illumination step of the second face of the object with a fluorophore excitation light and a second sequential acquisition step of a second series of images by detecting light emitted by the first face of the object. Reconstruction of the three-dimensional fluorophore distribution image in the object is performed by means of the first and second series of images.

9 Claims, 2 Drawing Sheets

U.S. PATENT DOCUMENTS

| | | |
|---|---|---|
| 5,148,022 A | 9/1992 | Kawaguchi et al. |
| 5,628,314 A | 5/1997 | Kumagai |
| 5,787,887 A | 8/1998 | Klingenbeck-Regn |
| 5,876,339 A | 3/1999 | Lemire |
| 6,081,322 A | 6/2000 | Barbour |
| 6,615,063 B1 * | 9/2003 | Ntziachristos et al. ...... 600/312 |
| RE38,800 E | 9/2005 | Barbour |

OTHER PUBLICATIONS

Addrige et al., Optical Tomography in Medical Imaging, *Inverse Problems*, No. 15, 1999, pp. R41-R93.

Ntziachristos et al., Charge-coupled-device Based Scanner for Tomography of Fluorescent near-infrared probes in Turbid Media, *Medical Physics*, AIP, Melville NY, vol. 29, No. 5, May 2002, pp. 803-809.

Markell et al., Effects of Sampling and Limited Data in Optical Tomography, *Applied Physics Letters*, vol. 81, No. 7, 2002.

Markell et al.., Dual-Projection Optical Diffusion Tomography, *Optics Letters*, vol. 29, No. 17, 2004.

Graves et al., Singular-value Analysis and Optimization of Experimental Parameters in Fluorescence Molecular Tomography, *Journal of Optical Society of America*, vol. 21, No. 2, 2004.

\* cited by examiner

METHOD AND DEVICE FOR RECONSTRUCTING A THREE-DIMENSIONAL FLUORESCENCE OPTICAL TOMOGRAPHY IMAGE BY DOUBLE MEASUREMENT

BACKGROUND OF THE INVENTION

The invention relates to a method for reconstructing a three-dimensional fluorescence optical tomography image to examine a plate-shaped object having a first face and an opposite second face and comprising fluorophores, said method comprising:
- a first illumination step for a sequential illumination of the first face of the object with a fluorophore excitation light from a plurality of lighting points, the first illumination step comprising a succession of illumination phases from a lighting point associated with each phase, and
- a first acquisition step for a sequential acquisition of a first series of images, an image of said series being formed, at each illumination phase of the first face, by a detector comprising a plurality of detection points simultaneously detecting light emitted by the second face of the object.

STATE OF THE ART

Fluorescence diffuse optical tomography (fDOT) consists in determining the three-dimensional distribution of fluorophores in an object comprising a homogenous diffusing medium. The fluorophores can be functionalized to target tumoral cells and to thereby mark cancerous cells. The article "Comparison of imaging geometries for diffuse optical tomography of tissue" by B. W. Pogue et al. (Optics Express Vol. 4, No. 8, 1999) compares different diffuse optical tomography (DOT) geometries.

When the object is in the form of a plate or slab (slab geometry), a front face of the object is illuminated by an excitation light having a spectrum corresponding to the fluorophore. The excitation light is then moved point by point on the surface of the object and a camera takes a series of images of the fluorescence light which is emitted by the rear face of the object. This geometry in which the opposite front and rear faces constitute two substantially parallel planes is frequently used in mammography and small animal imagery.

As represented very schematically in FIG. 1, object 1 is illuminated by a set of light sources S having an excitation wavelength λex placed in a same plane facing a first face 2 of the object 1. The light transmitted at the excitation wavelength λex and the light emitted by fluorophores 4 with an emission wavelength λem are detected by a set of detectors D arranged in one and the same plane facing a second face 3 of the object 1, opposite first face 2. In practice, the set of sources can be replaced by a laser, whose beam moves over first face 2 of the object 1. The object is then illuminated sequentially from each of the lighting points formed by each of the sources or each of the positions of the laser.

Excitation wavelength λex and emission wavelength λem are detected separately through optical filters. The signals Uex(s,d) detected at excitation wavelength λex and signals Uem(s,d) detected at emission wavelength λem can thereby be distinguished, s and d being the indices respectively identifying source S and detector D corresponding to signal U(s,d), i.e. source S and detector D activated for acquisition of signal U(s,d). An image, or more generally, signals representative of an image, are provided by the set of detectors at each illumination phase by one of the lighting points.

Processing of signals Uex(s,d) and Uem(s,d) enables a three-dimensional image of the distribution of fluorophores 4 in object 1 to be reconstructed from a series of sequentially acquired images respectively corresponding to illumination of the object by one of the lighting points. The algorithms for solving this problem are known and described for example in the article "Optical tomography in medical imaging" by S. R. Arridge (Inverse Problems 15, R41-R93, 1999). The problem is in particular solved on the basis of the diffusion equation established from the radiative transfer equation. Each source S generates a diffuse wave having the wavelength λex in the medium. The diffuse waves propagates in the medium and a part of the energy of the diffuse wave excites fluorophores 4 which can be considered as secondary sources reemitting a radiation at emission wavelength λem.

The diffusion equation is solved by means of Green's functions in a parallel planes geometry, which enables an analytical expression to be obtained for propagation of the diffuse wave in the medium.

As far as the fluorescence signal is concerned, each fluorophore 4 is considered to present a photon conversion parameter corresponding to the incident energy fraction that is remitted with emission wavelength λem. In a more general manner, a conversion parameter $X(m)$ can be associated with each volume element M (voxel) of object 1, where m is the grid meshing index identifying voxels M which are defined according to any mesh of the volume of object 1. The Green's function corresponding to light propagation between a voxel M and a detector D is noted $G(m,d)$. The Green's function corresponding to light propagation between a source S and a voxel M is further noted $G(s,m)$. The incident flux in voxel M corresponding to source S is proportional to $Q(s)G(s,m)$, where $Q(s)$ is the flux emitted by source S. The flux reemitted by voxel M with emission wavelength λem is given by $Q(s) G(s,m)X(m)$. The contribution of voxel M excited by source S to the signal detected by detector D is therefore proportional to $Q(s)G(s,m)X(m)G(m,d)$. Considering the whole volume of the object, signal Uem(s,d) is proportional to the sum of the contributions of all the voxels M, i.e. to the expression $Q(s) \Sigma m(G(s,m)X(m)G(m,d))$. When flux $Q(s)$ emitted by sources S are constant and equal for the different sources, the different constants can be incorporated in conversion parameters $X(m)$ and we obtain:

$$U_{s,d}^{em} = \sum_m G_{s,m} X_m G_{m,d}. \quad (1)$$

A linear system of equations is thereby obtained linking the measurements from the detectors with unknown conversion parameters $X(m)$ that are sought for.

Acquisition of a sufficient number of measurements thereby enables the distribution of fluorophores 4 in object 1 to be reconstructed. Reconstruction proper is for example performed by means of an iterative algorithm of ART (Algebraic Reconstruction Technique) type which minimizes the error between the experimental measurements and the computed analytical result.

The ART algorithm minimizes the error $$\left\| \frac{U_{s,d}^{em}}{U_{s,d}^{ex}} - \frac{\sum_m G_{s,m} X_m G_{m,d}}{U_{s,d}^{ex}} \right\|^2 = \| Y_{mes} - W X_m \|^2, \quad (2)$$

with $W = G(s,m)G(m,d)/Uex(s,d)$.

The fluorescence excitation light and the fluorescence light are usually situated in the near-infrared spectral band, as the penetrating power of this light is relatively high in biological tissues. The extinction coefficient being for example 2.5 cm$^{-1}$, the light intensity is reduced by a factor 12 for each centimeter penetrated, which excludes any study in a depth of more than 10 cm.

As the object presents a certain thickness, the fluorophores are not all at the same distance either from the light source or from the detectors, which leads to a loss of precision in the image reconstruction. The zones of the object situated near the plane of the light sources are in fact imaged with a lesser quality than those which are near the plane of the detectors, as indicated in the article "Effects of sampling and limited data in optical tomography" by V. A. Markel et al. (Applied Physics Letters Vol. 81, No. 7, 2002).

The article "Dual-projection optical diffusion tomography" by V. A. Markel et al. (Optics letters Vol. 29, No. 17, 2004) proposes using two orthogonal projections to improve the depth resolution with respect to the transverse resolution, which does not enable objects to be examined in the form of a slab with a thickness of about one centimeter and a width and height that are substantially greater than one centimeter. The article "Singular-value analysis and optimization of experimental parameters in fluorescence molecular tomography" by E. E. Graves et al. (J. Opt. Soc. Am. Vol. 21, No. 2, 2004) studies the optimal distributions of light sources and detectors for parallel planes geometry.

Furthermore, in the case where the set of detectors is constituted by a camera, the number of individually lit points is often much smaller than the number of pixels of the camera. This resolution difference on each side of the object leads to a difference of precision in the thickness of the reconstructed volume.

OBJECT OF THE INVENTION

The object of the invention is to remedy these shortcomings, and in particular to improve the resolution of reconstruction of a three-dimensional image of the distribution of fluorophores in a diffusing medium having the form of a plate.

According to the invention this object is achieved by a method and device according to the appended claims.

The method according to the invention is more particularly characterized by the fact that, the density of the lighting points being lower than the density of the detection points, the method then comprises:

a second illumination step for a sequential illumination of the second face of the object with an excitation light of the fluorophores, a second acquisition step for a sequential of a second series of images by detection of light emitted by the first face of the object and reconstruction of the three-dimensional image of the distribution of the fluorophores in the object by means of the first and second series of images.

BRIEF DESCRIPTION OF THE DRAWINGS

Other advantages and features will become more clearly apparent from the following description of particular embodiments of the invention given as non-restrictive examples only and represented in the accompanying drawings, in which.

DESCRIPTION OF PARTICULAR EMBODIMENTS

The invention relates to a parallel planes geometry, the object 1 typically having a thickness comprised between 10 and 15 mm. A set of light sources S constituting a series of discrete lighting points for illumination of the object is preferably formed by a laser source which is moved in a plane parallel to the object in two orthogonal directions in order to grid object 1. The laser typically describes a grid of 11 by 15 positions with a pitch of 3 mm in this plane. Depending on the precision to be obtained, the pitch can be reduced and, depending on the size of the zone to be observed, the number of points can be increased (for example about 30 points or more in both directions).

The set of detectors is preferably formed by a CCD camera coupled with a lens to detect an image of the object in a plane parallel to the surface of object 1. The camera thereby acquires one image for each position of the laser source. More precisely, when the object is sequentially illuminated from the different lighting points, the camera provides a series of corresponding images acquired sequentially.

The intrinsic resolution of the image is determined by the size of the detection pixels and by the enlargement of the optical system. The images are then generally re-sampled to limit the number of detection points and consequently the computing time. Typically, re-sampling is performed with a pitch four times smaller than that of the sources. On outcome, 16 times more detection points than source points are thereby obtained. Thus, more particularly when a pixelated CCD camera comprising a dense matrix of detection points is used, a non-negligible dissymmetry exists between the relatively low density of the lighting points and the higher density of the detection points. This dissymmetry causes a dissymmetry in the depth resolution of the reconstructed image (along an axis perpendicular to the plane of the faces of the object).

The invention takes advantage of this dissymmetry to improve the resolution of the final three-dimensional image.

Figure 1:
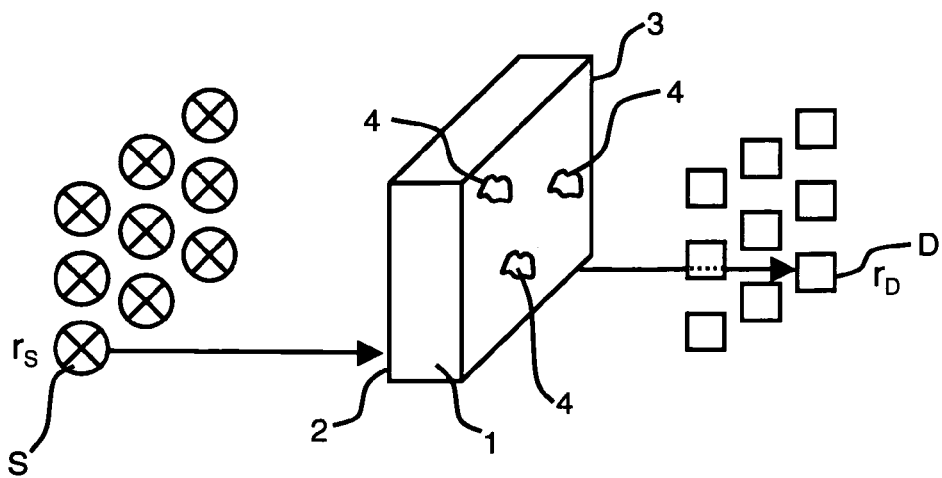
FIG. 1 illustrates a reconstruction method according to the prior art.
Figure 2:
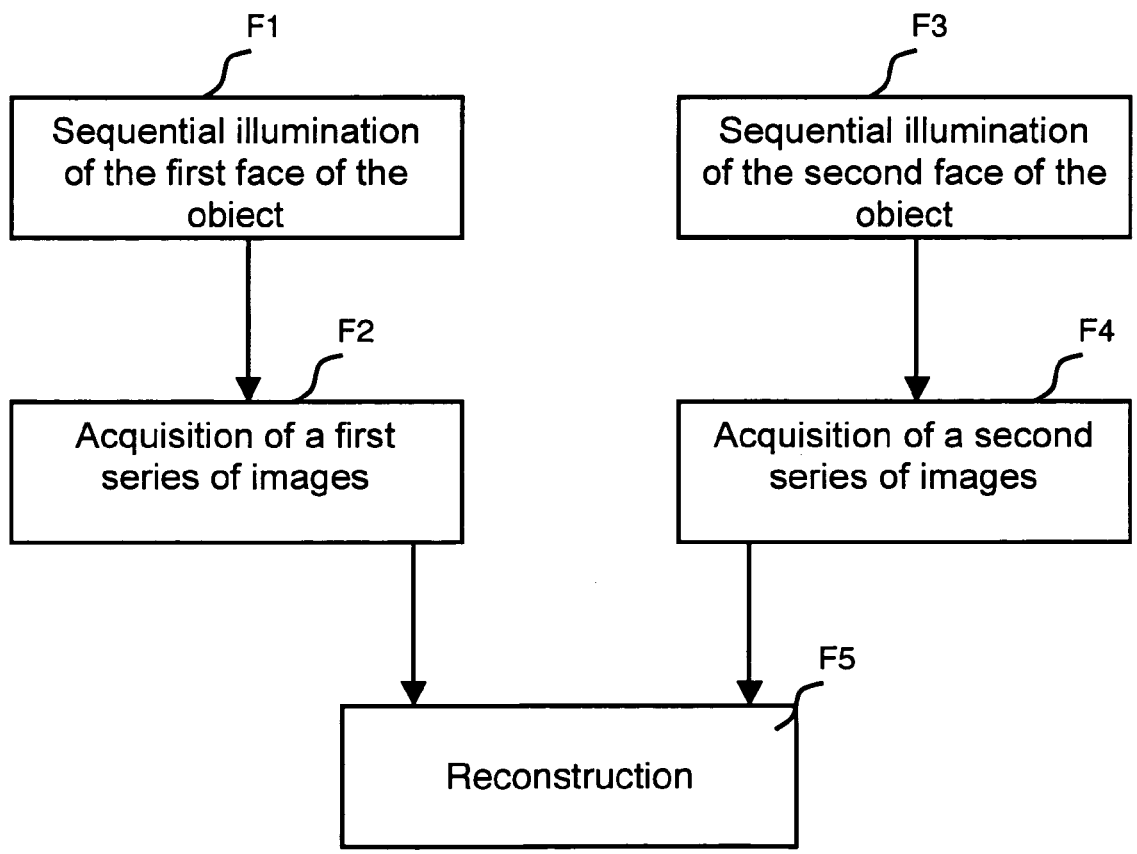
FIG. 2 schematically shows different steps of a reconstruction method according to the invention.

As illustrated in FIG. 2, a first sequential illumination step (F1) of first face 2 of object 1 is performed with a fluorophore excitation light having an excitation wavelength λex. In known manner, a first series of images is acquired (F2) during a succession of illumination phases by detection of a light emitted by second face 3 of object 1, which can comprise excitation wavelength λex and emission wavelength λem of fluorophore 4. As before, an illumination phase consists in lighting the object from a corresponding lighting point.

The image reconstruction method according to the invention comprises a second sequential illumination step (F3) consisting in lighting second face 3 of object 1 with a fluorophore excitation light having an excitation wavelength λex. As before, the illumination step comprises a succession of illumination phases each consisting in lighting the second face of the object from a corresponding lighting point.

A second sequential acquisition step of a second series of images (F4) is associated with the second illumination step. During the succession of corresponding illumination phases of second face 3, the second sequential acquisition step detects the light emitted by first face 2 of object 1, which can comprise excitation wavelength λex and emission wavelength λem of fluorophore 4. Reconstruction (F5) of the distribution of fluorophores 4 in object 1 is performed by means of the first and second series of images.

Advantageously, the light emitted by first face 2 and the light emitted by second face 3 are filtered to eliminate the excitation light. Only emission wavelength λem of fluorophore 4 is therefore detected.

When reconstruction is performed, the different zones of object 1 therefore benefit from a high resolution due to one of the two image acquisition steps and due to reversal of the measurement. The resolution is no longer limited by the thickness of object 1.

To reconstruct the image of object 1 by means of the first and second series of images, the linear system described above is completed using two sets of matrixes of the Green's functions corresponding respectively to the first and second acquisition of series of images. At each iteration of the ART algorithm, instead of only considering a single linear system, the set of equations formed by both systems is considered. Reconstruction of a three-dimensional image of the fluorophore distribution in the object is thus performed by establishing two linear systems of equations from two respective sets of matrixes of Green functions which are merged into one.

The first and second linear system of equations respectively associated with the first and second acquisition of series of images (F2 and F4) can be written as equation 1 above. A super measuring index i=i(s,d) can be defined containing the indexes s and d of the light sources and detectors, for example according to the relation i=Nd.s+d, where Nd is the number of detectors. With W(i,m)=G(s,m)G(m,d), each system is then written:

$$U_i^{em} = \sum_m G_{s,m} X_m G_{m,d}, \quad (3)$$

which is equivalent to the matrix systems $U_1=W_1 X$ and $U_2=W_2 X$. The two systems corresponding respectively to the two image acquisitions are then combined writing:

$$\begin{bmatrix} U_1 \\ U_2 \end{bmatrix} = \begin{bmatrix} W_1 \\ W_2 \end{bmatrix} [X], \text{ or in symbolic form } U = WX, \quad (4)$$

where U is a matrix with a single column and 2n lines, W is a matrix with m columns and 2n lines and X is a matrix with a single column and m lines, with n=Nd.Ns (Ns is the number of sources). As defined above, m is the meshing index. The equations of the two systems can be considered sequentially or be rearranged in random manner.

Measurement according to the invention is in particular less sensitive to the movements of fluorophores 4 of object 1, for example caused by movement of the whole object 1, as in the case of breathing. In the parallel planes geometry according to the prior art, a moving fluorophore located near the sources is in fact less well reconstructed than a moving fluorophore located near the detectors. Using acquisition of two sets of images by reversal not only enables this imbalance to be palliated, but in addition enables the resolution to be improved over the whole thickness of the object 1.

Processing of the first and second series of images enables an improved result to be obtained compared with the prior art, even if the first and second series of images are processed independently. A zone close to one of surfaces 2 or 3 of object 1 is thereby always well resolved due to the one of the first and second series of images for which the detector is located near the zone. Simulations have shown that it is still possible to further improve the resolution of the reconstruction method by means of the combined processing of the first and second series of images. The two linear system of equations are then preferably combined to be solved.

Figure 3:
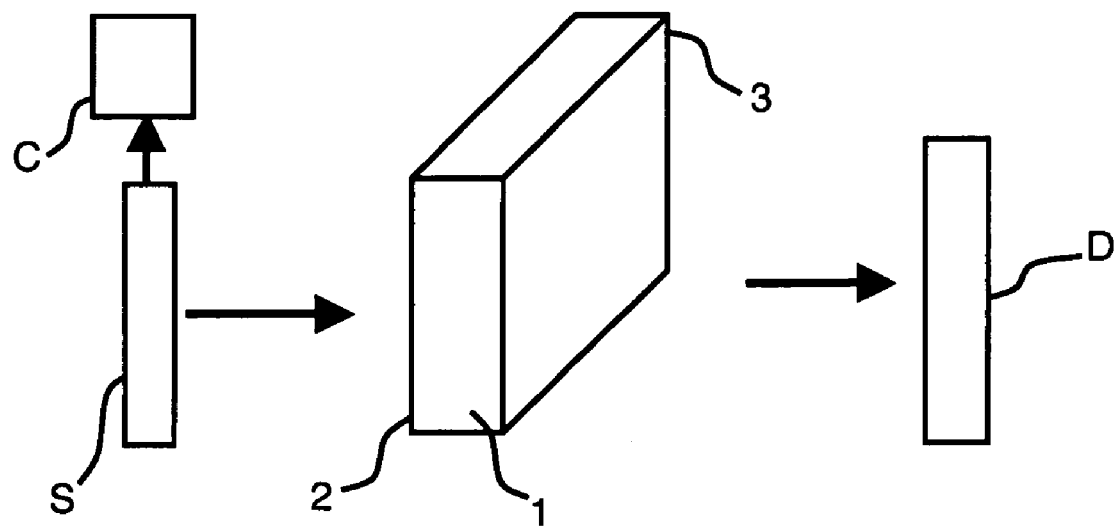
FIGS. 3 and 4 illustrate a particular embodiment of the method according to the invention.

The method can be implemented by means of a device comprising light sources S for illuminating first face 2 of object 1 with an excitation light λex of fluorophores 4, as represented in FIG. 3. The device further comprises a detector D, preferably a camera, for acquisition of a first series of images by detection of a light emitted by second face 3 of object 1. Detector D preferably comprises a filter to eliminate excitation light λex and is connected to a computing unit C. The device also comprises a source for illuminating second face 3 of object 1 with an excitation light λex of fluorophores 4. A second detector can be used for acquisition of a second series of images by detection of a light emitted by first face 2 of object 1. The two detectors are then connected to a computing unit C for reconstruction of a three-dimensional image of the distribution of fluorophores 4 in object 1 by means of first and second series of images.

The first and second illumination steps (F1, F3) can be performed with a same light source S and the acquisition of the two series of images by one and the same detector. In a first particular embodiment, light source S and object 1 are moved relatively between the first and second illumination steps. In the example illustrated in FIGS. 3 and 4, light source S and detector D are moved, whereas object 1 remains unmoved. It can also be envisaged to turn object 1. In a second particular embodiment, not represented, the excitation light can be directed onto first (2) and second (3) faces of object 1 by means of one or more mirrors.

Figure 4:
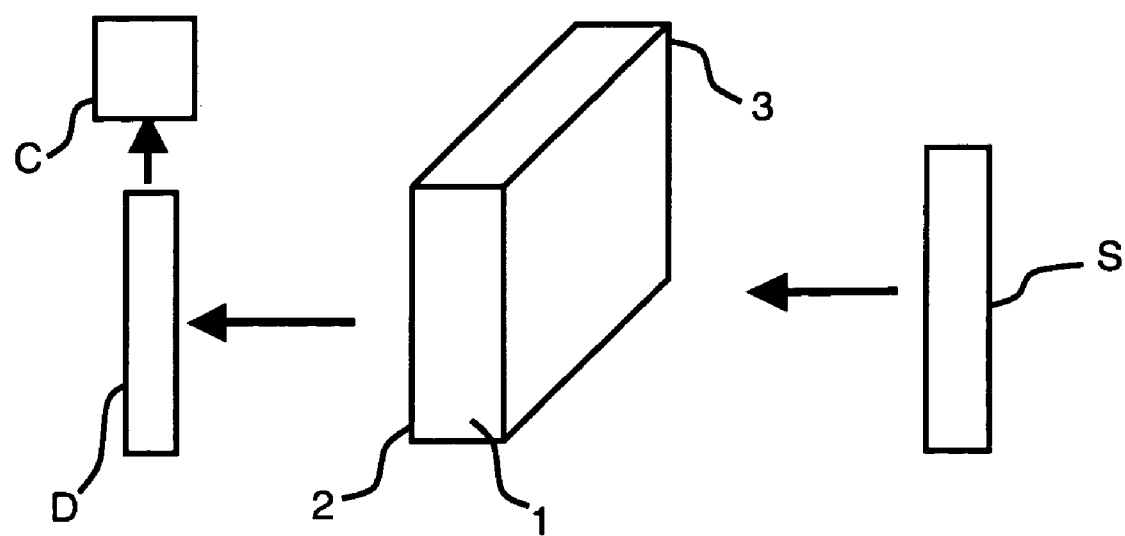

The first and second image acquisition steps (F2, F4) can thus be performed with one and the same camera. The camera constituting detector D is then for example moved as represented in FIGS. 3 and 4, or the object is turned as described above. For image acquisition it can also be envisaged to direct the light coming from the first (2) and second (3) faces onto the camera by means of one or more mirrors.

It should be noted that acquisition of the second series of images obtained by transmission through the object illuminated from its second face does not enable the precision of the final image to be improved if the density (number and distribution) of the lighting points and of the detection points is equivalent. This would in fact quite simply correspond to a transposition of matrices G(s,m).

The method according to the invention applies to any object in the form of a plate or able to be made to take such a shape, in particular a compressed breast. The term 'image' used to designate the images provided by the detector moreover covers the signals representative of an image.

The invention claimed is:

1. A method for reconstructing a three-dimensional fluorescence optical tomography image to examine a plate-shaped object having a first face and an opposite second face and comprising fluorophores, said method comprising:

a first illumination step for a sequential illumination of the first face of the object with an excitation light of the fluorophores from a plurality of lighting points, the first illumination step comprising a succession of illumination phases from a lighting point associated with each phase, and a first acquisition step for a sequential acquisition of a first series of images, an image of said series being formed, at each illumination phase of the first face, by a detector comprising a plurality of detection points simultaneously detecting light emitted by the second face of the object, the density of the lighting points being lower than the density of the detection points, a second illumination step, comprising a succession of illumination phases, for a sequential illumination of the second face of the object with a fluorophore excitation light, a second acquisition step for a sequential acquisition of a second series of images, an image of said second series being formed, at each illumination phase of the second face, by detection of light emitted by the first face of the object and reconstruction of the three-dimensional image of the distribution of the fluorophores in the object by means of the first and second series of images.

2. The method according to claim 1, wherein the light emitted by the first face and the light emitted by the second face are filtered to eliminate the fluorophore excitation light.

3. The method according to claim 1, wherein the first and second illumination steps are performed with the same light source the light source and the object being moved relatively between the first and second illumination steps.

4. The method according to claim 1, wherein the first and second illumination steps are performed with the same light source the excitation light (lex) being directed onto the first or second faces by means of at least one mirror.

5. The method according to claim 1, wherein the first and second acquisition steps of series of images are performed with one and the same camera, the camera and the object being moved relatively between the first and second image acquisition steps.

6. The method according to claim 1, wherein the first and second acquisition steps of series of images are performed with one and the same camera, the light coming from the first and second faces being directed onto the camera by means of at least one mirror.

7. The method according to claim 1, wherein the reconstruction of the distribution of fluorophores in the object is performed by establishing two linear systems of equations from two respective sets of matrixes of Green's functions.

8. The method according to claim 7, wherein the two linear systems of equations are combined to be solved.

9. A device for implementation of the reconstruction method according to claim 1, comprising:

means for sequential illumination of the first face of the object, from the plurality of lighting points, with a fluorophore excitation light, means for sequential acquisition, by means of the detector comprising said plurality of detection points, of the first series of images by detection of a light emitted by the second face of the object, the density of the lighting points being lower than the density of the detection points, means for sequential illumination of the second face of the object with a fluorpohore excitation light, means for sequential acquisition of a second series of images by detection of light emitted by the first face of the object and means for reconstruction of a three-dimensional image of the distribution of the fluorophores in the object by means of the first and second series of images.

* * * * *